United States Patent [19]

Hauschild et al.

[11] 4,443,564

[45] Apr. 17, 1984

[54] PACKAGED SPECKLED DENTIFRICE

[75] Inventors: John P. Hauschild, Bridgewater; Joseph R. Principe, East Brunswick, both of N.J.

[73] Assignee: Colgate-Palmolive Company, New York, N.Y.

[21] Appl. No.: 413,195

[22] Filed: Aug. 30, 1982

Related U.S. Application Data

[62] Division of Ser. No. 307,272, Sep. 30, 1981, Pat. No. 4,376,762.

[51] Int. Cl.³ .............................................. A61K 7/16
[52] U.S. Cl. ...................................... 523/105; 524/46; 424/49; 222/107
[58] Field of Search ................. 523/105, 120; 524/46; 424/49; 222/107

[56] References Cited

U.S. PATENT DOCUMENTS

| | | | |
|---|---|---|---|
| 3,297,207 | 4/1964 | Ballin | 222/107 |
| 3,929,988 | 12/1975 | Barth | 424/49 |
| 3,935,306 | 1/1976 | Roberts et al. | 424/49 |
| 4,139,665 | 2/1979 | Herrero | 222/107 |
| 4,376,763 | 3/1983 | Barth et al. | 424/7.1 |

*Primary Examiner*—John Kight, III
*Assistant Examiner*—Nathan M. Nutter

*Attorney, Agent, or Firm*—Robert L. Stone; Murray M. Grill; Herbert S. Sylvester

[57] ABSTRACT

Functional agglomerated speckles, for incorporation in dentifrices, include agglomerates of a water insoluble powdered functional material and a mixture of a water insoluble, ethanol soluble ethyl cellulose binder and a suitable water soluble binder, such as polyvinyl pyrrolidone. Such speckles, while more "soluble" or disintegrable in a flavored dentifrice than those based on ethyl cellulose binders without PVP, still can satisfactorily maintain their integrity and identity during processing of the dentifrice after addition of the speckles to the main dentifrice body, but on storage, after packaging of the dentifrice in dispensing tubes, they will soften sufficiently so as then to be essentially impalpable to one utilizing the dentifrice in brushing his teeth. Despite such softening the speckles continue to maintain their identity as separate small bodies in the dentifrice. The invented speckles are especially useful in translucent or transparent gel dentifrices, which contain components, such as flavoring and surface active agents, which may controllably soften the speckles on storage. Also described in the specification are dentifrices incorporating the present speckles, methods for manufacturing the speckles and such dentifrices, and such dentifrices packaged in end use dispensing containers.

18 Claims, 1 Drawing Figure

U.S. Patent    Apr. 17, 1984    4,443,564

Fig. 1

PACKAGED SPECKLED DENTIFRICE

This application is a division of co-pending application Ser. No. 307,272, filed Sept. 30, 1981, which was issued as U.S. Pat. No. 4,376,762 on Mar. 15, 1983.

This invention relates to functional agglomerated speckles for incorporation in dentifrices. More particularly, it relates to such speckles and to dentifrices containing them, wherein the speckles are made from a water insoluble powdered functional material, such as a dental polishing agent, a water insoluble, ethanol soluble ethyl cellulose binder, and a suitable water soluble binder, such as polyvinyl pyrrolidone. The invention also relates to methods for manufacturing such speckles and such dentifrices and to such dentifrices packaged in dispensing containers, such as transparent or translucent containers, through the wall of which the speckles, in a transparent or translucent gel dentifrice, may be viewed. To obtain desired visual effects the speckles will usually be of a color which contrasts with the rest of the dentifrice.

Prior art toothpastes and gels which incorporated contrastingly colored speckles are known. Although such speckles in some cases are primarily for aesthetic effects, they may be based on functional components, such as polishing agents, and they can perform desired functions in the dentifrice, in addition to making it of attractive appearance. Various colors and combinations thereof in the speckles may serve to identify the particular type of dentifrice, such as fluoride and non-fluoride dentifrices. Incorporation of reactive materials in the speckles can help to prevent reaction or premature reaction with other dentifrice components. When the speckles comprise mostly water insoluble material, such as a polishing agent, they can be present in a transparent or translucent gel dentifrice without objectionably clouding the gel. Thus, the gel remains clear, with the speckles being visible therein, and the speckles provide a decorative and aethestically improved appearance for the product.

In the past various speckled dentifrices have included speckles which were initially palpable but became impalpable during toothbrushing. Although such products have met with technical approval it has also been found desirable to market another type of speckled dentifrice, like that of this invention, in which the speckles, although readily visible and discrete, are impalpable initially and subsequently during brushing of the teeth.

Among the various prior art references showing dentifrices incorporating speckles and other similar dispersed solids therein, the closest to the present invention that are known to applicants are U.S. Pat. No. Re. 29,634; U.S. Pat. Nos. 3,929,988; 4,003,971; 4,089,943; and 4,220,552. The reissue patent describes a dentifrice containing visible and palpable, substantially water-insoluble, agglomerated particles of polishing agents. Binding agents are employed in the manufacture of the described speckles, and among the water soluble binders methyl cellulose and PVP are mentioned. However, methyl cellulose and PVP are water soluble and therefore do not provide a speckle which will always sufficiently and easily maintain its integrity during lengthy processing and also eventually soften to an impalpable unit on storage in a dentifrice. U.S. Pat. No. 3,929,988 relates to a dentifrice containing encapsulated sweetener. Ethyl cellulose is mentioned among various other materials useful for coating the sweetener to make the capsules or spheres, which may be visible or "microsize", and are dispersed in the dentifrice. U.S. Pat. No. 4,003,971 teaches making dentifrice speckles and describes the advantages of water insoluble binders for such speckles. The patent mentions the use of gums as water insoluble binders but does not disclose or suggest ethyl cellulose. U.S. Pat. No. 4,089,943 teaches toothpaste formulations having dispersed therein visible agglomerated particles of dental polishing agent. The advantages of both water soluble and water insoluble agglomerating or binding agents are mentioned in the patent, PVP is disclosed and mixtures of water soluble and water insoluble binders in the speckles are suggested, but ethyl cellulose is not mentioned as being useful as a binder. Finally, U.S. Pat. No. 4,220,552 teaches microencapsulation of sodium fluoride by lower alkyl cellulose, such as ethyl cellulose, and dispersing of the capsules in a dentifrice. The patent does not relate to agglomerates and the employment of ethyl cellulose of an encapsulating agent does not make obvious its present use with PVP to make an agglomerating agent useful in making the present speckles.

The present invention is one wherein ethyl cellulose, which is water insoluble but ethanol soluble, and a water soluble binder, preferably PVP, are utilized together to make an agglomerating agent for a functional water insoluble powdered material which is made into dentifrice speckles of improved properties. Prior speckles, made with water soluble binders, such as methyl cellulose or PVP, could disintegrate during processing after mixing in with other dentifrice components, such as those in previously formulated gel or paste media, if the speckled dentifrice was held too long in the processing equipment, which can happen, as when mechanical breakdowns of processing equipment occur. Such losses of integrity of the speckles could take place because such dentifrices contain water, which can solubilize the water soluble binders of the speckles and lead to separation of the component particles of the speckles. The dissolving of the binder can be minimized in such cases by prompt processing but when filling line holdups cause processing times to be increased losses of product could result. Dentifrice speckles made with ordinary water insoluble binding agents, as disclosed in the art (such art does not disclose ethyl cellulose), when dispersed in dentifrice gels or pastes, tend to be palpable, and although that may often be desirable, in some dentifrices, e.g., those intended for use by persons with sensitive gingiva, it is not. The combination of ethyl cellulose and PVP employed as a binder for functional speckles in accordance with the present invention satisfactorily maintains the integrity of the speckles in aqueous dentifrice media for a sufficiently long time to allow processing after incorporation of the speckles in the dentifrice. Yet, apparently due to the presence of PVP, which tends to dissolve in water, and because of the action of components of the dentifrice, such as flavoring agents, and in some cases, surface active agents, which tend to soften the ethyl cellulose of the speckles on storage, the speckles in the dentifrice may be softened sufficiently during storage so that, although they maintain their integrity and independence and their distinctly separate appearance until they are used, they are impalpable and are readily disintegrated during toothbrushing. In this respect the speckles of this invention function like those described in the patent application of Barth and Norfleet, Ser. No. 307,273, filed Sept. 30, 1981, which was issued as U.S. Pat. No. 4,376,763 on Mar. 15, 1983, in which ethyl cellulose is the water insoluble binder for the speckles. However, the PVP makes the speckles more useful in dentifrices containing lesser proportions of flavoring agents (and dental detergent and any other solvents or lipophiles) or in those dentifrice in which such materials are of lower solubilizing (for ethyl cellulose) properties.

In accordance with the present invention functional agglomerated speckles, for incorporation in dentifrices, comprise agglomerates of water insoluble powdered functional material, a water insoluble, ethanol soluble ethyl cellulose binder and a water soluble binder. Preferably, the functional material is a dental polishing agent and comprises 75 or 80 to 98% of the speckles, the water soluble binder is PVP and the combination of ethyl cellulose and PVP comprises 2 to 20% of the speckles. Optionally, the speckles may include a coloring agent, which may be 0 to 5% thereof, more preferably 0.05 to 1%, when present. Also claimed in this application are a dentifrice containing such speckles, methods for the manufacture of the speckles and of the dentifrice, and a packaged gel dentifrice containing the invented speckles dispersed therein.

The invention will be readily understood from the present specification, including the detailed description therein. However, in accordance with the Statute and Rules of Practice a drawing of a packaged dentifrice of this invention is also provided and the figure thereof will be described.

The functional agglomerated speckles are comprised of two essential components, a water insoluble powdered functional material and a combination of a water insoluble, ethanol soluble ethyl cellulose binder and a water soluble binder. Henceforth in this specification, for clarity and because PVP is a preferred water soluble binder, it will often be recited instead of "water soluble binder" but such designation is intended to refer to all suitable water soluble binders that can at least partially replace it in the invented speckles, while the desired properties of the speckles will still be obtained. Some other such binders will be listed later herein. The water insoluble powdered functional material may be characterized as the functional bodying agent and the ethyl cellulose-PVP combination is called the binder. Various functional materials, all of which are preferably water insoluble, or at least, slowly soluble, can be employed, including colorants, such as pigments, germicides, ion exchange agents, polymeric materials (which may contain other active components, sometimes water soluble materials), and flavorings, but it is highly preferred that the functional base material for the speckles be a polishing agent or include a major proportion thereof. Of the polishing agents, normally utilized in dry powder form to make the agglomerated speckles, those preferred are salts or oxides, such as dicalcium phosphate, tricalcium phosphate, insoluble sodium metaphosphate, alumina, silica, magnesium carbonate, calcium carbonate, calcium pyrophosphate, bentonite and zirconium silicate, and suitable mixtures thereof. Both anhydrous or calcined forms of these materials, such as calcined alumina, and hydrated forms, such as dicalcium phosphate dihydrate, may be employed but the anhydrous or calcined materials are often preferred. Because the agglomerates will normally desirably be opaque there is no need to match refractive indices with those of the dentifrice vehicles (including other components, too) but "transparent" polishing agents, with such a matching refractive index, e.g., 1.44 to 1.47, may be used to make transparent or translucent speckles, and they may also be employed to make clear gel dentifrice bodies containing polishing agent. Such "transparent" polishing agents include colloidal silicate and those sold under the trademark Syloid, as Syloids 63, 66, 72 and 74, under the mark Santocel, as Santocel 100 and as Zeo's 49, 113 and 119 and Zeodent. Also, synthetic alkali metal aluminosilicate complexes may be particularly useful, because they have refractive indices close to those of dental vehicles including water, glycerol, sorbitol and gelling agent, which materials are normally employed in the manufacture of dentifrices.

The water insoluble, powdered functional material utilized to make the present speckles will normally be of initial particle sizes in the range of 0.5 to 20 microns, preferably being within the range of 1 to 10 microns, and more preferably of 2 to 8 microns. However, in some instances larger particles sizes may be employed, as when the agglomerating operation tends to size-reduce some of the powder, as may happen in mixing before actual agglomerating begins.

The water insoluble component of the binding agent for the present speckles is ethyl cellulose. This effective binder is soluble in ethanol, and is gradually soluble in an aqueous glycerol-sorbitol medium which also contains "solvents" for it, such as flavorings and surfactants, which are usually present in the dentifrices of this invention. Such ethyl cellulose will usually have an ethoxy content in the range of about 45 to 50%, preferably 48 to 50% or 48 to 49.5%. In a preferred ethyl cellulose, such as that marketed by The Dow Chemical Company under the trade name Ethocel Standard 10 Premium Ethyl Cellulose, the ethoxy content is in the range of 48.0 to 49.5%; the viscosity is 9 to 11 centipoises; the moisture content is 2% maximum; chloride content, as NaCl, is 0.15% maximum; and ash content is 0.15% maximum. The test methods employed for the foregoing analyses are those incorporated in Test D914 of the American Society For Testing Materials (ASTM). Because the ethyl cellulose is intended for oral use the maximum content of arsenic, as $As_2O_3$, is three parts per million (p.p.m.), that of lead is 10 p.p.m. and that of heavy metal is 40 p.p.m., all by Food Chemicals Codex (FCC) testing.

In the 18-page Dow Chemical Company booklet entitled ETHOCEL Ethylcellulose Resins-Tough, Rugged Coatings, Adhesives, Hot Melts, copyrighted 1974, 1975 and 1978, hereby incorporated by reference, suitable ethyl cellulose resins for use as binders for the present speckles are described. Ethyl cellulose is supplied commercially as a white to light tan granular powder of a degree of etherification such that there are 2.25 to 2.58 ethoxy groups per anhydroglucose unit, which corresponds to 45.0 to 49.5% ethoxy content (by weight). Of two grades of ethyl cellulose commercially available the "standard" materials, which are preferred for the practice of the present invention, have ethoxy contents in the range of 48.0 to 49.5% (by weight), and the less preferred "medium" materials have ethoxy contents in the 45.0 to 46.5% range. Of course, such products are available in different viscosity ranges, usually from 3 to 110 centipoises, with the medium material tending to be more viscous.

The standard grade of ethyl cellulose tends to be soluble in aromatic hydrocarbons, hydroaromatic hydrocarbons, chlorinated aliphatic hydrocarbons and naval stores. It is also soluble in monohydric aliphatic alcohols, such as ethanol; monohydric cyclic alcohols, such as benzyl alcohol, phenyl ethyl alcohol and pine oil; ether alcohols, such as glycol ethers; ethers, such as diethyl cellosolve; esters, especially acetates, such as isopropyl acetate and sec-amyl acetate, and esters of hydroxy acids, such as methyl salicylate; and ketones, such as cyclohexanone and acetophenone. Generally, the medium ethoxy grade of ethyl cellulose is less soluble than the standard grade and so may be more suited for use with PVP when greater proportions of solubilizing materials are present in the dentifrice formula. However, in some such instances one could use the standard ethyl cellulose alone as a binder, as is taught in the Barth-Norfleet patent, previously mentioned.

Among other physical properties of ethyl cellulose are: a specific gravity of about 1:1; a water absorption after twenty-four hours immersion of about 1%; an impact strength, expressed as energy to break, of about 1 to 12 ft. lbs./sq. in. of notch; a tensile strength of about 6,000 to 9,000 lbs./sq. in.; an elongation of about 10 to 40%; a Rockwell hardness of about 70 to 110; a compression molding temperature of about 320° to 350° F.; a compression molding pressure of about 300 to 6,000 lbs./sq. in.; and a specific heat of about 0.3 to 0.46. Ethyl cellulose is heat stable, light stable, colorless, odorless and tasteless.

The water soluble binders which are useful for making the combination binder utilized for production of the speckles of this invention include, among others, gum acacia; gelatin; starches, both natural and modified; alkali metal carboxymethyl celluloses, particularly sodium carboxymethyl cellulose; polyethylene glycols; sugars, such as glucose and sucrose; methyl cellulose; carboxyethyl hydroxyethyl celluloses; alginates, particularly sodium alginate; polyvinyl alcohol; carrageenan, preferably Irish moss; xanthan gums; gum tragacanth; and PVP. It has been found the PVP is stable in the presence of ethyl cellulose, does not bleed excessively from the speckles in which it is incorporated as a binder in combination with ethyl cellulose, and lends itself to use to adjust the binding properties of the combination binder, so as to make such binder readily adaptable for employment in the same desired total proportion in a variety of dentifrice formulations, wherein the proportion of ethyl cellulose to PVP may be adjusted accordingly. Also important is the characteristic of the combination binder in the invented speckles of being sufficiently hard and firm so that during processing the speckles do not dissolve excessively and yet are sufficiently softenable on storage in the dentifrice in which they are incorporated so that they become impalpable by the time the dentifrice is used. They do not soften excessively so as to cause streaking in the tube or during discharge, but by adjustment of the proportion of ethyl cellulose to PVP, increasing the PVP, controlled streaking, if desirable, may sometimes be obtained.

PVP will usually be of molecular weights in the 30,000 to 50,000 range and the PVP preferably employed in the present invention is of a molecular weight of about 40,000. Such a product, which is marketed by GAF Corporation under the trademark Plasdone, as Plasdone K 29-32 and K 26-28, has average molecular weights designated by indicated K values, with K-30 being equivalent to about 40,000. PVP is available as a light colored powder containing less than 5% moisture, 12.6±0.4% of nitrogen, less than 2 parts per million of arsenic and less than 20 p.p.m. of heavy metals. It is soluble in cold water and in a variety of organic alcohols, acids, ether-alcohols, ketone-alcohols, chlorinated hydrocarbons, esters and ketones, but is insoluble in hydrocarbons and some ethers, chlorinated hydrocarbons, ketones and esters. It is compatible with various natural and synthetic resins, inorganic salts and with many synthetic organic detergents, including those commonly employed as dental detergents, e.g., sodium higher fatty alcohol sulfate and poly-lower alkoxylated alcohol sulfates.

Although it might have been expected that the best speckles would be made from the least soluble binder material, it has been found that the combination of ethyl cellulose and water soluble binder, preferably PVP, as described in this invention, makes speckles of ideal properties, which maintain their individuality and integrity to a satisfactory extent while being processed and during storage, but which are also essentially impalpable during use of the dentifrice in brushing the teeth. If desired, the character of the speckles may be changed, as by varying the proportions of the ethyl cellulose and PVP, modifying the degree of ethoxy content of the ethyl cellulose, changing the molecular weight of the PVP and/or by blending with the combined binder other substantially water insoluble and/or water soluble binders of known types, some of which are mentioned in the patents previously referred to, the disclosures of which are incorporated herein by reference. The properties of the speckles may also be regulated by adjusting the proportions of functional material and the binder, as will be referred to subsequently, and such is an advantage of this invention. Thus, agglomerates may be made which will be stable during processing after mixing, such as deaerating and filling, yet which will break up rapidly after the dental cream is extruded from its container or, if desired, such breaking up may be retarded so that the agglomerates will feel harder and somewhat firmer to the user during brushing of his teeth. Of course, it is normally highly preferable for the speckles to be substantially impalpable on use, while still maintaining their identity in the dentifrice.

The binder will normally be of particle size like that of the functional powdered material of the speckles, especially if the agglomerates are to be made, at least in part, by compacting of powdered materials. However, because normally the speckles will be made by utilizing an alcoholic solution of the binder components, the particle sizes thereof are of relatively little importance.

The speckles, while sometimes white or colorless and possibly even translucent or transparent, or approaching such appearances, may also be colored, normally due to containing a suitable proportion of dye or pigment or a mixture of dyes and/or pigments. Any nontoxic dye or pigment of a suitable color, usually a strong color, such as one of a suitable hue, with a Munsell chroma greater than 4 and a Munsell value in the 4 to 7 range, may be utilized and in some instances weak colors or pastels may be satisfactory or desirable. It is usually best to employ a dye or pigment which is approved for drug and cosmetic use (D&C) or for food, drug and cosmetic use (FD&C). Representative of suitable dyes are D&C Reds No's 2, 3, 6, 7, 8, 9, 10, 11, 12, 13, 19, 30, 31, 36 and 37; D&C Blue No. 1; FD&C Blues No's 1 and 2; FD&C Reds No's 1, 2 and 3; FD&C Yellow No. 5; cosmetic green oxide; and cosmetic red oxide. Pigments of the foregoing dyes, known as lakes, are also suitable for use in coloring the speckles but normally the dyes will be preferred. The mentioned pigments are often composed of dyes supported on a finely powdered insoluble carrier, and the pigments are dispersed rather than dissolved in the medium to be colored. The particle sizes of pigments employed may be within the range previously given for the polishing agents or may be sized like the binder. Sizes may be finer, e.g., in the 0.01 to 1 micron range. Particle sizes of dyes may be similar but because they are normally employed in dissolved state, in water or solvent, preferably being oil soluble and being dissolved in the appropriate solvent, sizes are not important as long as the powder or particles are small enough so as to make the dye readily soluble in the solvent chosen.

The speckles of this invention may be made by suitable methods, either wet or dry processes. Employing a wet granulation process, the binder components, in dry powder form, are first preferably blended with polishing agent and dye or pigment, if present, and ethanol or equivalent solvent. Water and/or lipophilic solvent may be present with the ethanol and a dye or pigment for coloring the speckles may also be present. Alternatively, an ethanol solution of the binder may have a suitable dye or pigment and the polishing agent admixed with it. Preferably, the PVP and the polishing agent are pre-mixed, both being in powder form, the ethyl cellulose is dissolved in alcohol, the solution is used to "moisten" the powder, and the speckles are made by the "wet granulation method". The proportions of components employed will be such as to result in speckles of the desired composition and the proportion of solvent(s) will normally be from 5 to 50% of the mix, preferably 5 to 25% thereof.

The production of the dispersion may be by means of a Hobart mixer, Dravo pan, or other suitable mixing device or granulator for wetting powder(s), and the order of addition of the various components of the dispersion may be adjusted as best befits the mixing or blending apparatus employed although the preferred method described above appears to give best results, avoiding gummy overconcentrations of binder, and uniformly dispersing the two binders throughout the polishing agent. A preferred way of producing the speckles is by forcing the "wetted" mix of polishing agent and ethyl cellulose (with dye or pigment, if present) through a screen having uniform openings, which usually will be in the range of about 150 to 2,000 microns (about in the No. 10 to 100 sieve range, U.S. Sieve Series) and the "extruded" agglomerates are then dried, usually either in air or in an oven. Instead of screens, other means, such as pressure extruders, may be employed for extruding or otherwise pelletizing the mix, after which the particles resulting are dried. The particles are then classified into desired size ranges, normally in the No's. 10 to 80 range, preferably No's. 40 to 80 and more preferably No's. 30 to 60 (U.S. Sieve Series). Of course, if the wet mass is formed in a Dravo pan the forced screening or other extruding may be omitted. Generally, when the particle sizes are larger than 2,000 microns (No. 10 sieve) they will be less satisfactory for introduction into the oral cavity of a user and when less than about 177 microns in diameter (No. 80 sieve) they will not be as readily apparent and hence, will not be of as attractive an appearance.

Instead of employing the wet granulation process a dry or slugging process may be utilized, wherein the components of the speckles may be pressed to large tablet size and such tablet may then be broken up, with particles thereof in the desired size range being separated from the others. In such tableting process it may be desirable to employ a water insoluble lubricant, such as talc, magnesium stearate, calcium stearate or stearic acid, which also helps to facilitate agglomeration. Similarly, such materials and other water insoluble adjuvants may be present when wet granulation methods are used. The speckles made are preferably dry, containing no moisture, but moisture contents of up to 10%, e.g., 1 to 5%, may be present without causing any serious adverse effects on the properties of the speckles.

The proportions in the speckles of water insoluble powdered functional material, such as dental polishing agent, and the combination binder will be such that the binder will be the minor component of the speckles and the powdered functional material will be the major component thereof (although allowance should be made for the presence of other materials too, such as colors and adjuvants). Generally, the dental polishing agent or functional material is from 75 or 80 to 98% of the speckles, preferably 85 to 97% thereof, the binder combination will be 2 to 20% of the speckles, preferably 3 to 15% thereof and the colorant will be 0 to 5% of the speckles, such as about 0.05 to 1% thereof, all on a dry basis, free of water and ethanol or other solvent. The binder combination will be one in which the proportion of ethyl cellulose to PVP is in the range of 1:10 to 10:1, preferably 1:5 to 5:1, more preferably 1:2, to 2:1, and most preferably 1:2 to 1:1, e.g., 2:3.

The dentifrice in which the speckles are distributed may be any suitable such product, because in the present invention it acts primarily as the medium for the speckles, maintaining them independent, individual and separate, while performing its normal dentifrice functions. Opaque dentifrices are useful media for the present speckles but it is highly preferred that the dentifrice be transparent or translucent and normally be of a type characterized as a gel. Dentifrices normally comprise water, humectant, gelling agent, dental detergent and a dental polishing agent, usually with flavoring and/or coloring, too. Among various functional adjuvants are fluorides, stabilizers, anti-caries agents and antibacterial compounds.

The water employed will preferably be deionized water, although city waters, both soft and hard, may also be utilized. The gelling agent is normally a water soluble natural or synthetic gum or gum-like material, among which are carrageenan, gum tragacanth, xanthan gum, alginates, alkali metal carboxymethyl cellulose (preferably sodium carboxymethyl cellulose), hydroxymethyl carboxyethyl cellulose, polyvinyl pyrrolidone, starch, and hydrophilic colloidal carboxyvinyl polymers, such as those sold under the trademarks Carbopol 934 and 940. Although various polyols may be utilized as humectants those preferred are of 3 to 6 carbon atoms and 3 to 6 hydroxyls per molecule, and those of choice are glycerol and sorbitol. The glycerol is in normal liquid state, generally being about 99% or more pure, and sorbitol, normally being a solid, is frequently utilized as a 70% aqueous solution thereof (70% sorbitol, 30% water). The three mentioned components may be considered as the main constituents of the dentifrice vehicle, in which flavor and detergent may also be incorporated. Such detergent may include a soap but normally will be a non-soap synthetic organic surface active agent having detersive properties. Preferably such detergent will be of the anionic type, although nonionic detergents are also useful, ampholytic detergents can be employed, and cationic detergents can be acceptable under some circumstances.

The preferred anionic detergents are especially useful because they combine excellent cleaning action and foaming properties. Normally, such compounds include hydrophilically and lipophilically balanced moieties, with the lipophilic moiety usually being a higher fatty alkyl or acyl of 10 to 18 carbon atoms, preferably 12 to 16 carbon atoms, and the hydrophile being alkali metal, e.g., sodium, potassium, or ammonium or lower alkanolammonium. Suitable such anionic detergents are: the water soluble salts (normally alkali metal and preferably sodium or potassium) of higher fatty acid monoglyceride sulfates, such as the sodium salt of the monosulfated monoglyceride of hydrogenated coconut oil fatty acids; higher alkyl sulfates, such as sodium lauryl sulfate; alkylaryl sulfonates, such as sodium linear dodecyl benzene sulfonate; higher alkyl sulfoacetates; higher fatty acid ester 1,2-dihydroxypropane sulfonates; the sodium salts of sulfated polyethyoxylated alcohols; and the substantially saturated higher aliphatic acylamides of lower aliphatic aminocarboxylic acid compounds, such as N-lauroyl sarcosine, and the sodium, potassium and ethanolamine salts of N-lauroyl-, N-myristoyl-, and N-palmitoyl sarcosine, all of which sarcosine compounds are preferably substantially free from soap or similar higher fatty acid material. Among the nonionic detergents, ethoxylated sorbitan monostearate, with approximately 20 mols of ethylene oxide per mol; condensates of ethylene oxide with propylene oxide and propylene glycol (Pluronics); polyethoxylated higher fatty alcohols, such as the Neodols (23-6.5 and 45-11, for example); and condensation products of alpha-olefin oxides containing 10 to 20 carbon atoms, polyhydric alcohols containing 2 to 10 carbon atoms and 2 to 6 hydroxyl groups, and either ethylene oxide or heteric mixtures of ethylene oxide and propylene oxide, are useful. Quaternized imidazoyl derivatives, such as Miranol $C_2M$, and other Miranols represent useful amphoteric detergents and the quaternary ammonium halides, such as dimethyl dicetyl ammonium bromide, represent cationic detergents.

The various polishing agents, which are dispersed in the dentifrice vehicle (or vehicle plus detergent and any other adjuvants) are those previously described for conversion to speckle form. Also useful in such group of materials are synthetic finely divided silicas, such as those sold under the trademarks Cab-O-Sil M-5, Syloid 244, Syloid 266, Aerosil D-200, Zeosyl 200 and Zeothix 265, which are normally utilized for only a small percentge of the polishing agent, normally being no more than 1 to 9% by weight of the total dentifrice, and which are useful for thickening or gelling the vehicle and improving the clarity of the dentifrice.

The dentifrices of this invention will normally contain suitable flavoring and/or sweetening materials, Examples of flavors include the flavoring oils, such as those of spearmint, peppermint, wintergreen, sassafras, clove, sage, eucalyptus, cinnamon, lemon and orange, and the sweetening agents include sucrose, lactose, maltose and saccharin. Desirably for fluoride dentifrices there will also be present sodium fluoride, stannous fluoride, potassium fluoride, potassium stannous fluoride, sodium hexafluorostannate, stannous chlorofluoride and/or sodium monofluorophosphate.

The flavoring materials include various well known essential oils, mainly: terpenes; esters; alcohols; aldehydes; ketones; and other aromatic substances, many of which emit aromtic odors and fragrances. Because flavor is a simultaneous physiological and psychological response obtained from the presence of a substance in the mouth and depends on the senses of taste, smell and feel, with smell often being of primary importance, it is not surprising that aromatic materials are important components of flavors. In the present instances advantage is taken of this fact and of the chemical natures of such materials which, as was previously indicated in the discussion of solubilities of ethyl cellulose, permit the ethyl cellulose binder in the present speckles to be slowly solubilized by the solubilizing substances in the flavoring material, causing softening of the speckles but not causing their disintegration. For Example the terpenes, which are hydrocarbons and which constitute an important class of perfumery or flavor materials, are good solvents for the ethyl cellulose of this invention, as are many other flavoring materials, such as those previously named (as flavoring) oils) above, and others well known to the perfumery and flavoring arts. By utilizing the flavoring essences in the dentifrice composition to soften the combination binder of the speckles and thereby make them impalpable, which is an aim of this invention, it is unnecessary to add another component to the dentifrice or to the speckles for this purpose. Also, because of the relatively small proportion of flavoring material normally present in a dentifrice, with the proportion of the lipophilic part of the flavor often being lower, a desirable slow softening of the speckle particles can result, usually due to a relatively low mass transfer rate for the "solvent" material, which transfer rate is especially slowed due to the gelatinous nature of the dentifrice. Thus, even if some flavoring material at the interface with the speckle started to soften the ethyl cellulose thereof while the dentifrice was being blended, the flavor solution of ethyl cellulose would soon become saturated and this would inhibit further quick dissolving of the ethyl cellulose. Still with the passage of the normal time a dentifrice spends in storage before sale and use, which time will often be at least about 2 weeks and sometimes more (with certain dentifrice formulas it is desirable to allow them to age to improve flavor and product uniformity), the speckles become impalpable, yet remain distinct. Of course, in the above discussion, while references were made to the ethyl cellulose binder, it is recognized that the PVP binder is also present and is soluble in water. Nevertheless, the ethyl cellulose holds the speckle together in the presence of the PVP until it is solubilized by the lipophiles in the dentifrice, and the PVP allows less ethyl cellulose to be incorporated in the speckles and facilitates the softening of the speckles in dentifrices containing lesser proportions of solubilizing flavoring.

Although it is considered that the flavoring materials, particularly the lipophiles, which exert substantial solvent action on ethyl cellulose, are the most important slowly solubilizing components of the present dentifrice, the surface active agent component, which includes a lipophilic moiety, may also have an appreciable solubilizing effect and by means of its wetting action, may promote mass transfer in a dentifrice tube and thereby increase the solubility rate of the ethyl cellulose. It is also possible that combinations of other constituents of the dentifrice, including some of the sweetening agents and vehicle components, will further assist in solubilization of the ethyl cellulose to the extent desired, while not promoting premature softening of the speckles.

Colorants, such as those previously mentioned with respect to the speckles, may be employed, normally in lesser proportion, so as to provide a base which contrasts with the speckles. Various other adjuvant materials may be present in the dentifrice, including preservatives, silicones, chlorophyll compounds and ammoniated materials. Normally, when a gel dentifrice is made which is intended to be transparent or translucent, the polishing agent chosen will be one having an index of refraction closely matching that of the rest of the dentifrice medium. Of course, in such clear gel formulations the amount present of insoluble materials which would cloud the gel will normally be minimized. When the pH of the dentifrice is adjusted, and the pH is desirably within the range of 3 to 10, more desirably from 3.5 to 5 when stannous ions are present and 4.5 to 7 in the absence of such ions, organic acids, such as citric, malonic, and fumaric acids, may be employed.

In the dentifrice of this invention a dental polishing agent is uniformly distributed throughout the vehicle of water, humectant and gelling agent, with a dental detergent and the desired proportion of flavor already in it. Then the speckles, which also preferably contain a polishing agent (and often of a different type from that in the body of the dentifrice), are uniformly distributed throughout the dentifrice, usually comprising 0.1 to 10% of the dentifrice, preferably 0.5 to 5% thereof, more preferably 1 to 3% thereof and most preferably 1.5 to 2.5% thereof. The dental base will usually comprise: about 5 to 30% water, preferably 10 to 25% and more preferably 10 to 20%; about 20 to 70% of humectant, preferably polyol humectant, more preferably 45 to 65% thereof and most preferably 50 to 60% thereof; and about 0.1 to 5% of gelling agent, preferably 0.1 to 1% and more preferably 0.2 to 0.5% thereof. The humectant is preferably a mixture of glycerol and sorbitol wherein the glycerol content is 5 to 40% of the dental base, preferably 20 to 30%, and the sorbitol content is 5 to 50%, preferably 25 to 35%. The preferred gelling agent is sodium carboxymethyl cellulose, and a preferred proportion thereof utilized is about 0.3 to 0.4%. The dental detergent content will normally be from 0.5 to 5%, preferably 0.5 to 3%, and a preferred such detergent is sodium lauryl sulfate. The polishing agent in the dentifrice base, exclusive of that in the speckles, is normally 10 to 40%, preferably 15 to 30% and most preferably 20 to 25%, including Syloid 244 type silicas, which are also employed for thickening. Various other materials, including flavors (usually 0.5 to 2%), color, preservatives, sweeteners, and tooth hardeners (fluorides) will normally total no more than 10% of the dentifrice, preferably being from 2 to 7% thereof. Utilizing the proportions of the various constituents within the ranges given, with respect to the speckles and the medium in which they are distributed, results in an attractive product which is stable during storage and in which the speckles are uniformly and attractively distributed.

To prepare the speckled dentifrice, after first producing the speckles, is comparatively simple but an important consideration is that minimal mechanical agitation should be employed so as to prevent or delay any disintegration, softening and solubilization of the speckles in the dentifrice. It is considered that lipophilic materials and solvents present, such as those in flavoring oils, will slowly solubilize ethyl cellulose, but not to an objectionable extent in the absence of vigorous agitation in processing. If the dentifrice is at an elevated temperature during such mixing, normally due to manufacturing limitations in processing, it is even more important to minimize agitation. However, with the ethyl cellulose-containing binders that are used in the manufacture of the speckles, manufacturing restrictions may be less stringent, but care should still be exercised. Suitable equipments for distributing the speckles throughout the dentifrice include Banbury or dough mixers operated at low speeds but other gently operated blenders may also be used providing that mixing is controlled so as to prevent substantial breakdowns, dissolvings or disintegrations of the speckles. Normally mixing blade speed will be on the order of one to five r.p.m. and mixing will last from one to five minutes. After completion of the blending the dentifrice is deaerated and filled into containers, such as resilient or collapsible tubes. If vacuum is employed during mixing operations deaeration may be omitted.

The manufacturing method described in the preceding paragraph is a standard method for making speckled dentifrice, with the exception of the processing of the present speckles in such dentifrice and the requirement for the presence of slowly solubilizing lipophilic material in the base of the dentifrice, together with the speckles bound together by PVP-ethyl cellulose. However, recently new methods have been invented for facilitating blending of the speckles into the dental gel body without excessive agitation. Such methods and the apparatuses by means of which they are practiced are the inventions of Edward J. Gibbons and John Smith, respectively, and are the subjects of patent applications to be filed by them on the same date as the present application. In such methods the dentifrice is fed through an orifice to form a falling, curving ribbon onto which speckles are uniformly dropped at a constant rate, after the speckled gel dentifrice is transported to filling equipment by means of a positive displacement variable walled pump, such as one of the Moyno type.

Although normal collapsible aluminum tubes with capped dispensing openings, through which the dentifrice may be squeezed, are most commonly employed, it is often preferred to make the packaged dentifrice by utilizing a deformable tube of clear or translucent synthetic organic polymeric material, such as polyvinyl chloride, polyethylene, polyvinylidine chloride or similar material through which the attractive appearing speckled dentifrice may be viewed.

Figure 1:
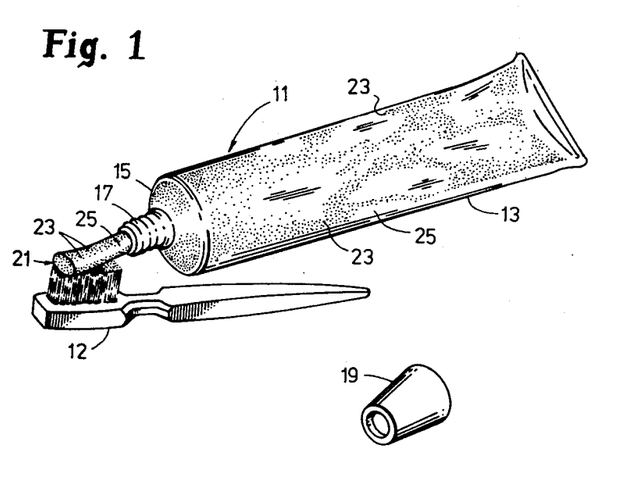

In FIG. 1 there is shown a plan view of the clear walled container 11, which is made of transparent polymeric material (PVC), including body 13, shoulder 15, threaded neck 17 and cap 19, with the cap having been removed from the tube. As illustrated, some of the dentifrice 21 is being dispensed from tube 11 through neck 17 onto the bristles of a toothbrush 12. In the dentifrice there are clearly shown invented speckles 23 in the continuous dentifrice medium 25. It is noted that such speckles are initially impalpable although they are easily visible. During toothbrushing they break down into smaller entities of essentially the same sizes as the component polishing agent. Of course, the speckle polishing agent acts together with that in the dental gel to help clean and polish the teeth.

The following examples illustrate but do not limit the invention. Throughout the specification, including the working examples, and in the claims, all parts are by weight, unless otherwise indicated.

EXAMPLE 1 (Actual)

95 Parts of calcined alumina (Microgrit WCA 9F) of particle size in the range of 0.5 to 10 microns and an average particle size in the range of 3 to 5 microns are blended with three parts of powdered polyvinyl pyrrolidone, obtained from GAF Corp., and marketed by them under the designation Plasdone K-29-32. Two parts of ethyl cellulose (10 centipoises), of the physical characteristics described previously in the specification and in powder form, are dissolved in five parts of ethanol (95%) and the PVP-alumina blend is mixed with the solution in a Hobart mixer. Mixing is continued for about four minutes until the blend is uniform, after which the mix is forced through a No. 10 (U.S. Sieve Series) screen, and the "extruded" material is oven dried for one hour at 60° C. The dried agglomerates are then screened through a No. 30 screen and the cut that rests on a No. 60 screen, the dried speckles comprising the calcined alumina, PVP and ethyl cellulose, is collected. The speckles produced are of angular shapes, with the ratios of maximum length to maximum width usually being within the 1 to 2 range and most of the particles being of such a ratio within the 1.1 to 1.5 range. The angularity of the particles may be a factor in making the dentifrices so attractive in appearance, at least for some consumers.

A transparent (or translucent) dentifrice base (all components except speckles) is made of the following formula:

| Component | Parts by Weight |
| --- | --- |
| Glycerol (99.3% pure) | 25.00 |
| Sodium carboxymethyl cellulose | 0.35 |
| Sorbitol (70% aqueous solution) | 39.04 |
| Polyethylene glycol 600 | 3.00 |
| Water | 3.00 |
| Sodium saccharin | 0.25 |
| Sodium benzoate | 0.50 |
| Blue dye (FD&C Blue No. 1, 1% aqueous solution) | 0.20 |
| Sodium monofluorophosphate (1 to 60 microns) | 0.76 |
| Silicon dioxide (Zeo 49) | 18.00 |
| Synthetic silica (Syloid 244) | 5.50 |
| Sodium lauryl sulfate | 1.20 |
| Flavor (spearmint, peppermint, wintergreen, clove, etc., as desired) | 1.20 |
|  | 98.00 |

Two parts of the described speckles, with particle sizes −30 +60 (U.S. Sieve Series), are gently blended in a slow moving mixer (about two r.p.m.) with 98 parts of the described dentifrice base, after which the mix is deaerated and automatically filled into capped collapsible tubes which are then sealed. During the mixing, dearation and tube filling steps the speckles, which are substantially evenly distributed through the dentifrice, remain discrete, independent and undissolved in the dentifrice base so that when the tube is opened, after filling, and preferably, after storage for about a month, and the dentifrice is squeezed through the discharge opening thereof, the speckles appear to have retained their initial integrity, contrasting with the bluish gel, in which they appear to be substantially evenly spaced, with no clumps or overconcentrations being readily apparent. When the product is evaluated immediately after filling, and without being stored, the speckles are palpable but, upon storage before use, for periods from two weeks to a year or more, are sufficiently softened, as by solubilization of the PVP by the moisture present and solubilization of the ethyl cellulose by the flavoring oil, both solubilizations apparently sometimes being with the aid of the dental detergent or other surface active agent that may be present, and sometimes assisted by other components too. The "solubilized" speckles appear distinct and are not "smeared"; yet they are satisfactorily impalpable. During toothbrushing with the dentifrice the speckle particles are readily reduced in size, are not irritating to gingiva, and are readily dischargeable from the oral cavity on completion of brushing.

Although the presence of the anionic detergent in the dental base may be of assistance, it is thought that the controlling component of such base is the 1.2% of flavoring agent present. A proportion of such an agent or a mixture thereof from 0.5 to 2%, preferably 0.8 to 1.5%, of which at least half is normally active as a solvent for ethyl cellulose, is desirable for best speckle dispersions, and the flavor will usually include over 50% and often over 80% of solubilizing hydrocarbons, esters, alcohols and aldehydes.

When the proportion of flavor in the dental gel base is decreased to 0.6%, half that of the above formula, the PVP-ethyl cellulose binder system for the speckles still is effective and they are satisfactorily impalpable on storage. It is also effective when the flavor concentration is varied to 0.3%, 0.9% and 1.5%. However, the greater proportions of flavor (and/or other lipophile solvents) may cause somewhat earlier solubilization than preferred, in which case the proportions of PVP and ethyl cellulose will preferably be varied, to 2 parts PVP and 3 parts ethyl cellulose, for example. Similarly, if the palpability of the speckles should increase to more than desired they may be made softer by increasing the PVP proportion, e.g., to twice the ethyl cellulose. The concentrations of speckles and the sizes thereof may be changed, within the ranges previously given. Also, others of the materials previously listed may be substituted for the alumina polishing agent, including other types of water insoluble functional substances.

The manufacturing method described for the dentifrice, in which the speckles are dispersed in the body of the gel, is one in which the mixing operation should be watched to make sure that the speckles are not disintegrating and, at any sign of this happening mixing should be halted and, providing that the dentifrice appearance is not significantly adversely affected, usually by being made unacceptably cloudy, filling of the tubes should be undertaken promptly. Instead of employing the described mixing method it will often be preferable to utilize the Gibbons or Smith methods, previously referred to herein, wherein a regulated even "fan" of speckles is deposited by means of gravity on a continuouly falling extruded ribbon of gel, to which the speckles adhere, so as to obtain uniformity of distribution of the speckles in the dentifrice. With respect to such processes and apparatuses the specifications and drawings of such patent applications are hereby included by reference.

When the speckled dentifrice of this invention is packed in a collapsible aluminum tube the speckles in the dentifrice are not visible until discharge from the tube but at that time they are maintained discrete in the toothpaste extruded and impart to it an attractive and distinctive appearance. However, when instead of the normal aluminum tubes one employs resilient transparent tubes, such as tubes of polyvinyl chloride or other suitable polymer, the speckles can be seen through the tubes and through the transparent gel dentifrice base, and their movements, on discharge, can be observed. This provides an additional aesthetic benefit and helps to make toothbrushing more interesting, at least for children. Additionally, the functional speckles act as a reminder to the person using the dentifrice of the presence of polishing agent or other functional constituent in the dentifrice and thereby help to remind him of the importance of brushing so that such component may be effective.

The formula given above is one for a gel dentifrice in which the normal 41.04% of sorbitol solution had been reduced to 39.04% to allow for the introduction of the 2% of speckles. The effect of this change in the formulation is to maintain the percentages of the other dentifrice components the same as in an unspeckled product, with the exception of the major component, the sorbitol solution. It is considered that with other variations in the contents of speckles in such dentifrices such procedure for modifying the formula may continue to be followed. However, it is also feasible to start with the initial gel formulation, e.g., containing 41.04% of sorbitol solution, and reduce each of the components proportionately to allow for the introduction of the desired percentage of speckles.

In a variation of the above described experiment 1% of ultramarine blue pigment may be employed in place of 1% of the Microgrit, so that the speckles are of a definite blue coloration. In place of the described proportion of ultramarine blue one may use 0.5 to 2.0% of that pigment or mixtures of pigment(s) and polishing agent(s) of proportions from 1:10 to 10:1 may be used. Alternatively, about 0.1 to 1% of any suitable water insoluble (or oil soluble) dye may be employed. In such cases the dye solution may be omitted from the dentifrice base formula or may be present, providing enough contrast between the speckles and the base is obtainable.

Of course, the various components of the formula may be replaced by others, such as those previously described, and useful products will also be obtained. For example, the different mentioned pigments and dyes may be employed, the sodium lauryl sulfate may be replaced by sodium ethoxylated higher fatty alcohol sulfate or sodium hydrogenated coconut oil fatty acids monoglyceride monosulfate, and the polishing agents may be replaced by dicalcium phosphate dihydrate and/or dicalcium phosphate (anhydrous) or mixtures thereof. Proportions of the various components may be modified ±10%, ±20%, and ±30%, so long as they are maintained within the ranges previously recited, and the results are satisfactory products of similar properties, although those of the proportions of this example are preferred.

EXAMPLE 2 (Actual)

75 Parts of anhydrous dicalcium phosphate and 15 parts of dicalcium phosphate dihydrate, both having average ultimate particle sizes of about 4 microns, are mixed with 5 parts of ethyl cellulose, 5 parts of PVP and 10 parts of ethyl alcohol in a Hobart mixer. Alternatively, and preferably, ethanol and ethyl cellulose may be premixed and then may be admixed with a previously made blend of the dicalcium phosphates with PVP. The mass formed is forced through a screen having uniform openings of 2,000 microns and is then oven dried for one hour at 60° C. The dried agglomerates are then screened through a screen having uniform openings of 420 microns and those agglomerates which do not pass through a screen having uniform openings of 177 microns are collected. Next, the agglomerated functional particles resulting are mixed with a dentifrice base of the formula given in Example 1, with the exception that the polishing agent in such base is replaced by sodium aluminosilicate, such as that marketed under the trade name Zeolite 4A.

In variations of this formula there may be substituted for the polishing agent of the speckles, hydrated alumina having an average particle size less than about 10 microns, calcium carbonate having particles substantially all of which are less than about 7.4 microns in diameter, insoluble sodium metaphosphate having an average particle size of about 5 microns (all such sizes being ultimate particle sizes), or a proportion of the polishing agent may be replaced by sodium monofluorophosphate of similar particle sizes.

The dentifrices of this example are speckled, transparent or translucent products and are aesthetically pleasing in appearance. The visible particles of the agglomerated polishing agents (for which other functional insoluble materials may be substituted in whole or in part) are substantially uniformly dispersed in the dentifrice base as visibly separate entities and are also essentially impalpable upon use, after storage. When the transparent gel is made opaque, as by incorporation therein of an opaque polishing agent, the speckles are still visible at the surface of the extruded dentifrice but the effect is not as striking.

EXAMPLE 3 (Theory)

The functional polishing agent constituent of Example 2 is replaced by a mixture of ten parts of anhydrous dicalcium phosphate and 90 parts of calcium carbonate, with the same total proportion of polishing agent being employed; otherwise the same procedure is followed. The products resulting are similarly satisfactory in functional effects and are aesthetically pleasing in appearance. Similar results are obtained when different mixtures of the disclosed polishing agents are substituted for the present mixture in the speckles, and when proportions thereof are varied.

EXAMPLE 4 (Theory)

Instead of dissolving the ethyl cellulose and PVP in ethanol or other suitable solvent, agglomerates like those of Example 3 are made by blending the polishing agent, PVP and ethyl cellulose, sometimes with a reduced proportion of ethanol present, to form a powder blend. Such blend is compressed in a rotary tablet press to form slugs, about 6 mm. thick and 25 mm. in diameter. The slugs are then granulated in an oscillating granulator to form smaller particles, preferably such as will pass through a No. 40 screen and rest on a No. 60 or No. 80 screen. This technique for making the speckles may also be applied to any of the speckle formulas given in the preceding examples. Although the binding effects of the PVP and ethyl cellulose might not be as great, the products of this example are also satisfactory for incorporation in dentifrices to contribute their aesthetic advantages and functional effects. If the binding effects of the PVP and ethyl cellulose in the foregoing formulas are not sufficient, the proportions thereof present may be increased, sometimes up to 100 or 200%, but such increases involve additional expenses and therefore the "wet" method, in which solutions of PVP and ethyl cellulose in ethanol or other suitable solvents are employed, is often preferred.

With respect to all the preceding examples, the manufacturer will take care to adjust the formulation to obtain the desired type of speckle, of the desired solubility or "resistance to solubility" in the dentifrice. This may be accomplished by choosing the binders, particularly the ethyl cellulose, in accordance with the amount of solubilizing materials, especially flavoring agent (and detergent and any other lipophile) present. For example, the medium ethyl cellulose previously mentioned may be employed when larger proportions of flavoring agent are present, with the standard ethyl cellulose being used for lesser amounts of the flavoring agent (and other lipophiles). Mixtures of the two and mixtures with ethyl celluloses of other characteristics may be made to obtain intermediate properties for the present combination PVP-ethyl cellulose binders. Also, the nature of the lipophilic portion of the dentifrice body may be adjusted, where possible, so as to increase or decrease solubilizing effects so that the suspended speckles behave in the desired manner, resisting early disintegration but becoming impalpable thereafter.

EXAMPLE 5 (Theory)

In the preceding examples, the polyvinyl pyrrolidone, the water soluble binder portion of the combination binder, is partially replaced (50%) or entirely replaced by the following water soluble binders: gum acacia, gelatin, corn starch, sodium carboxymethyl cellulose, sodium alginate, polyvinyl alcohol, carrageenan, xanthan gum and gum tragacanth. The speckles made, when incorporated in gel dentifrices like those previously described in these examples, sufficiently retain their individuality and integrity during processing but become impalpable on storage in the dentifrice, while still retaining their original shapes, in the same manner as the speckles made with PVP-ethyl cellulose combination binders. However, it is considered that the PVP-ethyl cellulose combination binder is generally superior in its combination of desirable features, including processing stability, compatibility with dentifrice components, and conversion from palpability to impalpability without loss of speckle integrity and without significant change in appearance.

EXAMPLE 6 (Actual)

(Comparative Example)

Speckles of various compositions are compared to those of this invention that are based on ethyl cellulose and PVP. The invented speckles are made in generally the manner as described in Example 1, by the wet method, and the speckle formula includes 95% of calcined alumina, 2% of ethyl cellulose and 3% of PVP with such materials being the same as those used in Example 1. The speckles of the comparative experiments are also made by the wet method, except for one type, which will be indicated, which was made by the dry or "slugging" method of Example 4.

The speckles were tested by weighing out 100 milligrams of each type, separately placing them on glass slides, adding to each four drops of water, covering each slide with another slide, and noting the time of physical change and the type of physical change in the granules. When 2% of sodium carboxymethyl cellulose is employed as the binder the speckles lose integrity within fifteen seconds, which is also the case with the speckles bound with 2% of hydroxypropyl methyl cellulose, but that takes two minutes. Speckles made with a binder comprising 2% of methyl cellulose and 3% of PVP soften, swell and lose integrity after about two minutes and when 5% of PVP is employed as the sole binder speckles made with it soften after eight minutes. When the binder is 1% of methyl cellulose (400 centipoises), the speckles lose integrity after a little more than five minutes and when the binder is changed to 10% of polyethylene glycol 6,000, with 1% of magnesium stearate, with the speckles being made by "slugging", they lose integrity after nineteen minutes. The "control" speckles of this invention, including 2% of ethyl cellulose and 3% of PVP, when subjected to the same test, are still intact after over six hours.

The results of this test clearly indicate the importance of the presence of ethyl cellulose with a water soluble binder, preferably with PVP.

The invention has been described with respect to various illustrations and embodiments thereof but is not to be limited to these because it is evident that one of skill in the art with the present specification before him would be able to utilize substitutes and equivalents without departing from the invention.

What is claimed is:

1. A packaged dentifrice comprising a dispensing container containing a dentifrice comprising water, humectant, gelling agent, detergent and flavor, all of which are constituents of a gelled vehicle of the dentifrice, and a dental polishing agent, uniformly distributed throughout the vehicle, and visible functional speckles distributed through the dentifrice, which are agglomerates of water insoluble powdered functional material and a combination of a water insoluble, ethanol soluble ethyl cellulose binder and a water soluble binder.

2. A packaged dentifrice according to claim 1 wherein the dentifrice is in the form of a transparent or translucent gel, with the speckles visible therein, in which the speckles comprise from 0.1 to 10% of the dentifrice, and the water soluble binder in the speckles is PVP.

3. A packaged dentifrice according to claim 2 wherein the speckles are comprised of a major proportion of dental polishing agent and a minor proportion of the combination binder, in which binder the ratio of ethyl cellulose to PVP is within the range of 1:5 to 5:1, and the speckles are impalpable and are of sizes in the No. 10 to No. 80 U.S. Sieve Series range.

4. A packaged dentifrice according to claim 3 wherein the speckles are 0.5 to 5% of the dentifrice and are comprised of 80 to 98% of dental polishing agent and 2 to 20% of the combination binder, in which binder the ratio of ethyl cellulose to PVP is within the range of 1:2 to 2:1, and the speckles are of sizes in the No. 30 to No. 80 sieve size range.

5. A packaged dentifrice according to claim 4 wherein the speckles are about 2% of the dentifrice, are comprised of about 95% of dental polishing agent and about 5% of the combination binder, and are of sizes in the No. 30 to No. 60 U.S. Sieve Series range.

6. A packaged dentifrice according to claim 4 wherein the dentifrice comprises 5 to 40% of glycerol, 5 to 50% of sorbitol, 5 to 30% of water, 0.1 to 5% of gelling agent, 0.5 to 5% of dental detergent, 0.5 to 2% of flavoring agent and 10 to 40% of water insoluble dental polishing agent in a continuous phase, and the speckles of which are comprised of 80 to 98% of a dental polishing agent which is an oxide or a salt selected from the group consisting of dicalcium phosphate, tricalcium phosphate, insoluble sodium metaphosphate, alumina, silica, magnesium carbonate, calcium carbonate, calcium pyrophosphate, bentonite and zirconium silicate, and mixtures thereof, and 2 to 20% of binder comprising ethyl celulose and PVP, and the proportion of speckles in the dentifrice is 1 to 3%.

7. A packaged dentifrice according to claim 6 wherein the dentifrice comprises 20 to 30% of glycerol, 25 to 35% of sorbitol, 0.1 to 1% of gelling agent, 1 to 5% of polyethylene glycol, 0.5 to 3% of sodium lauryl sulfate dental detergent, 0.8 to 1.5% of flavoring agent, 15 to 30% of a dental polishing agent selected from the group consisting of dicalcium phosphate and silicon dioxide, and mixtures thereof, and 10 to 25% of water, in a continuous phase, in which dentifrice the speckles comprise 90 to 97% of a dental polishing agent selected from the group consisting of anhydrous dicalcium phosphate, dicalcium phosphate dihydrate, tricalcium phosphate, zirconium silicate and calcined alumina, and mixtures thereof, and 3 to 10% of a binder consisting of ethyl cellulose of a degree of ethoxylation of 48 to 49.5% and PVP of a molecular weight averaging about 40,000, with the ratio of ethyl cellulose to PVP being within the range of 1:2 to 1:1, and in which the sizes of the speckles are in the No. 30 to No. 60 U.S. Sieve Series range and the proportion thereof in the dentifrice is from 1.5 to 2.5%.

8. A packaged dentifrice according to claim 1 wherein the dentifrice is a clear or translucent gel with opaque and impalpable speckles distributed throughout.

9. A packaged dentifrice according to claim 8 wherein the gel is clear.

10. A packaged dentifrice according to claim 9 wherein the dispensing container is a deformable tube of clear or translucent synthetic organic polymeric material.

11. A packaged dentifrice according to claim 10 wherein the deformable tube is of clear synthetic organic polymeric material.

12. A packaged dentifrice according to claim 11 wherein the deformable tube is of polyvinyl chloride.

13. A packaged dentifrice according to claim 3 wherein the dentifrice is a clear or translucent gel with opaque speckles distributed throughout.

14. A packaged dentifrice according to claim 13 wherein the gel is clear and the dispensing container is a deformable tube of clear or translucent synthetic organic polymeric material.

15. A packaged dentifrice according to claim 14 wherein the deformable tube is of polyvinyl chloride.

16. A packaged dentifrice according to claim 4 wherein the dentifrice is a clear or translucent gel with opaque speckles distributed throughout.

17. A packaged dentifrice according to claim 16 wherein the gel is clear and the dispensing container is a deformable tube of clear or translucent synthetic organic polymeric material.

18. A packaged dentifrice according to claim 17 wherein the deformable tube is of polyvinyl chloride.

* * * * *